United States Patent [19]

Sato et al.

[11] 4,248,779
[45] Feb. 3, 1981

[54] PROCESS FOR PRODUCING THIOLCARBAMATES

[75] Inventors: Zenichi Sato, Shimizu; Fumiya Tabuchi, Shizuoka; Keiichiro Takagi, Shizuoka; Yoji Imamiya, Shizuoka, all of Japan

[73] Assignee: Ihara Chemical Industry Company, Limited, Tokyo, Japan

[21] Appl. No.: 948,346

[22] Filed: Oct. 4, 1978

[30] Foreign Application Priority Data

Nov. 16, 1977 [JP] Japan .................................. 52/137424

[51] Int. Cl.³ .................. C07C 155/03; C07D 207/32; C07D 295/10; C07D 211/06
[52] U.S. Cl. ........................ 260/239 BF; 260/455 A; 260/326.4; 544/159; 544/158; 546/245; 546/237; 546/230; 546/235
[58] Field of Search .......... 260/455 A, 239 BF, 326.4, 260/293.85, 293.73; 544/159, 158; 546/245, 237, 230, 235

[56] References Cited

U.S. PATENT DOCUMENTS 3,954,729  5/1976  Sato ................................. 260/455 A

OTHER PUBLICATIONS

Tilles, Journal American Chemical Society, vol. 81, p. 714, (1959).
Derwent Abstracts 5226OU-C, abstract of Japananes Patent Publication No. 28427/1973.

Primary Examiner—Henry R. Jiles
Assistant Examiner—Robert C. Whittenbaugh
Attorney, Agent, or Firm—Oblon, Fisher, Spivak, McClelland & Maier

[57] ABSTRACT

A thiolcarbamate having the formula

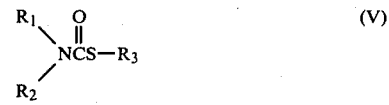
(V)

wherein $R_1$ and $R_2$ are the same or different and respectively represent an alkyl, alkoxy, alkenyl, cycloalkyl, hydroxyalkyl, phenyl or benzyl group and $R_1$ and $R_2$ can form a ring by binding each other with or without oxygen atom; and $R_3$ represents a lower alkyl or benzyl group or a substituted benzyl group having one or two substituent of halogen atom, alkyl, alkoxy, alkylthio, nitro, or cyano group, which comprises reacting carbonyl sulfide with a sec-amine having the formula

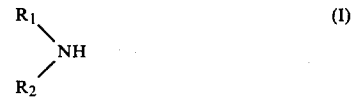
(I)

wherein $R_1$ and $R_2$ are defined above, in an aqueous medium and then reacting a halogenated hydrocarbon having the formula

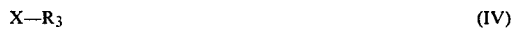

wherein $R_3$ is defined above and X represents a halogen atom, in an aqueous medium.

10 Claims, No Drawings

PROCESS FOR PRODUCING THIOLCARBAMATES

BACKGROUND OF THE INVENTION

The present invention relates to a process for producing thiolcarbamates which can be used as effective agricultural chemicals. More particularly, it relates to an improved process for producing thiolcarbamates by reacting carbonyl sulfide with a sec-amine and a halogenated hydrocarbon in an aqueous medium.

Heretofore, it has been known to produce thiolcarbamates by (1) a process for reacting a benzyl halide with an aqueous solution of an alkali metal salt of thiocarbamic acid in U.S. Pat. No. 3,144,475.

However, in the process, the benzyl halide which is reacted with the alkali metal salt of thiolcarbamic acid is water insoluble whereby the reaction of the benzyl halide with the aqueous solution of an alkali metal salt of thiolcarbamic acid is a heterogeneous reaction and the reaction is not smoothly performed to cause certain disadvantages of a long time for the reaction and low yield of the object product.

The following processes have been proposed as improved processes for producing thiolcarbamates to overcome the disadvantage in the process (1). (2) A process for reacting benzyl halide with the alkali metal salt of thiolcarbamic acid in a mixed solvent of water and acetone, methanol or ethanol. (Japanese Patent Publication No. 28427/1973.) (3) A process for reacting carbonyl sulfide with sec-amine in an organic solvent to produce an amine salt of thiolcarbamic acid and further reacting the product with an alkyl halide or benzyl halide. (Japanese Unexamined Patent Publication Nos. 88030/1975 and 78832/1977. ) (4) A process for reacting an alkyl halide with an aqueous solution of an alkali metal salt of thiolcarbamic acid in the presence of a catalyst of a quaternary ammonium salt, a quaternary phosphonium salt, a quaternary ammonium type resin or a quaternary phosphonium type resin. (Japanese Unexamined Patent Publication No. 108908/1977.)

That is, in the process (2), a water soluble organic solvent such as acetone, methanol and ethanol is used as the solvent for the reaction and the reaction of benzyl halide with an aqueous solution of an alkali metal salt of thiolcarbamic acid is performed in a homogenous system whereby the reaction is smoothly performed.

In the process (3), the reaction is performed by using amine salt of thiolcarbamic acid as the thiolcarbamic acid salt and using an organic solvent such as aliphatic hydrocarbons, aromatic hydrocarbons, halogenated hydrocarbons, N,N-lower dialkyl formamides, lower dialkyl sulfoxides, lower alkyl cyanamides, and nitrobenzenes as the solvent for reaction; to react an alkyl halide or a benzyl halide with the amine salt of thiolcarbamic acid in the organic solvent in the homogeneous system whereby the reaction is smoothly performed.

In the process (4), the reaction of an alkyl halide with an aqueous solution of an alkali metal salt of thiolcarbamic acid is smoothly performed by using a quaternary ammonium salt, a quaternary phosphonium salt a quaternary ammonium type resin or a quaternary phosphonium type resin as the catalyst.

However, in the process (2), the water soluble organic solvent such as acetone, methanol or ethanol is used whereby the contamination of the water soluble solvent into a drainage can not be prevented to cause an environmental pollution, disadvantageously.

In the process (3), the organic solvent is used whereby the recovery of the solvent is required from the viewpoints of cost and environmental safety whereby a recovery step is required disadvantageously. Moreover, in the process (4), the expensive water soluble quaternary ammonium salts, quaternary phosphonium salts, etc. are used as catalyst, whereby the contamination of the catalyst into the drainage can not be prevented to increase nitrogen content and phosphorus content in the rivers, seas or lakes and marshes and to cause the environmental pollution and it is economically disadvantageous and it requires a long reaction time, disadvantageously.

As described, the processes (2) to (4) are not suitable as the process for producing thiolcarbamates from the viewpoints of the requirements of environmental safety and non-pollution and low cost.

The inventors have studied to overcome the disadvantages by producing an aqueous solution of an amine salt of thiolcarbamic acid by reacting carbonyl sulfide with a sec-amine in an aqueous solution and then reacting a halogenated hydrocarbon with the amine salt of thiolcarbamic acid.

The inventors have found that the reaction of the amine salt of thiolcarbamic acid with the halogenated hydrocarbon is smoothly performed even though it is a heterogeneous reaction.

SUMMARY OF THE INVENTION

It is an object of the present invention to provide a process for producing thiolcarbamates in high efficiency by smoothly performing a heterogeneous reaction.

The foregoing and other objects of the present invention have been attained by providing a process for producing thiolcarbamate having the formula

(V)

wherein $R_1$ and $R_2$ are the same or different and respectively represent an alkyl, alkoxy, alkenyl, cycloalkyl, hydroxyalkyl, phenyl or benzyl group and $R_1$ and $R_2$ can form a ring by binding each other with or without oxygen atom; and $R_3$ represents a lower alkyl or benzyl group or a substituted benzyl group having one or two substituent of halogen atom, alkyl, alkoxy, alkylthio, nitro, or cyano group, which comprises reacting carbonyl sulfide with a sec-amine having the formula

(I)

wherein $R_1$ and $R_2$ are defined above in an aqueous medium and then reacting a halogenated hydrocarbon having the formula

wherein $R_3$ is defined above and X represents a halogen atom in an aqueous medium.

DETAILED DESCRIPTION OF THE PREFERRED EMBODIMENTS

The sec-amines used in the process of the present invention are the amines having the formula (I) wherein $R_1$ and $R_2$ are the same or different and respectively represent an alkyl, alkoxy, alkenyl, cycloalkyl, hydroxyalkyl, phenyl or benzyl group and $R_1$ and $R_2$ can form a ring by binding each other with or without oxygen atom.

The sec-amine whose $R_1$ and $R_2$ form a ring is a cyclic amine including a heterocyclic amine. The alkyl group can be $C_1$ to $C_{12}$ alkyl group.

Suitable sec-amines include symmetric sec-amines such as dimethylamine, diethylamine, di-n-propylamine, di-iso-propylamine, di-n-butylamine, di-iso-butylamine, di-n-amylamine, di-n-hexylamine, bis(2-ethylhexyl)amine, di-n-octylamine, diallylamine, bis(2-methylallyl)amine, dicyclohexylamine, diethanolamine, di-isopropanolamine, diphenylamine, and dibenzylamine; and asymmetric sec-amines such as N-methyl n-butylamine, N-ethyl n-butylamine, N-butyl ethanolamine, N-methyl phenylamine, N-ethyl phenylamine, N-methyl benzylamine, N-ethyl benzylamine and N-methyl cyclohexylamine; cyclic sec-amines such as pyrrolidine, piperidine, hexamethyleneimine and morpholine.

The halogenated hydrocarbons used in the process of the present invention are the alkyl halides or benzyl halides having the formula (IV) wherein X is a halogen atom such as Cl, Br and I and $R_3$ is a lower alkyl group such as methyl, ethyl, n-propyl, iso-propyl and n-butyl; benzyl group or a substituted benzyl group having one or two substituent of halogen atom, alkyl, alkoxy, alkylthio, nitro or cyano group.

Suitable halogenated hydrocarbons include alkyl halides such as methyl iodide, ethyl iodide, isopropyl iodide, n-propyl bromide, n-butyl iodide and iso-butyl bromide, and benzyl halides such as benzyl chloride, benzyl bromide, benzyl iodide; 2-, 3- or 4-fluorobenzyl chloride or bromide; 2-, 3- or 4-chlorobenzyl chloride or bromide; 2-, 3- or 4-bromobenzyl bromide; 2-, 3- or 4-iodobenzyl chloride, 2-, 3-, 4-methylbenzyl chloride or bromide; 4-ethylbenzyl chloride, 4-(isopropyl)benzyl chloride, 4-(isopropyl)benzyl chloride, 2-methoxybenzyl chloride, 3-ethoxybenzyl bromide, 4-(isopropoxy)benzyl chloride, 4-methylthiobenzyl chloride, 4-ethylthiobenzyl chloride, 2-, 3- or 4-nitrobenzyl chloride or bromide; 2-, 3- or 4-cyanobenzyl bromide; 2,6-dichlorobenzyl chloride or bromide; 4-chloro-2-methoxybenzyl chloride, 2-chloro-4-nitrobenzyl chloride or bromide, 2,5-dimethylbenzyl chloride, 4-methyl-3-nitrobenzyl chloride and 3,5-dinitrobenzyl chloride.

The thiolcarbamates produced by the process of the present invention are thiolcarbamates having the formula (V) wherein $R_1$ and $R_2$ are the same or different and respectively represent an alkyl, alkoxy, alkenyl, cycloalkyl, hydroxyalkyl, phenyl or benzyl group and $R_1$ and $R_2$ can form a ring by binding each other with or without oxygen atom and $R_3$ represents a lower alkyl, benzyl or a substituted benzyl group having one or two substituent of halogen atom, alkyl, alkoxy, alkylthio, nitro or cyano group.

Suitable thiolcarbamates include S-alkyl thiolcarbamates such as S-ethyl-N,N-diethyl thiocarbamate, S-ethyl-N,N-di-n-propyl thiolcarbamate, S-ethyl-N,N-hexamethylene thiolcarbamate; and S-benzyl or substituted benzyl thiolcarbamates such as S-benzyl-N,N-dimethyl thiolcarbamate, S-4-chlorobenzyl-N,N-diethyl thiolcarbamate, S-4-ethylbenzyl-N,N-dibenzyl thiolcarbamate, S-4-iso-propylbenzyl-N-ethyl-N-phenyl thiolcarbamate, S-2-methoxybenzyl-N,N-dimethyl thiolcarbamate, S-4-ethoxybenzyl-N,N-hexamethylene thiolcarbamate, S-4-methylthiobenzyl-N,N-tetramethylene thiolcarbamate, S-4-ethylthiobenzyl-N,N-diallyl thiolcarbamate, S-4-nitrobenzyl-N,N-bis(2-hydroxyethyl) thiolcarbamate, S-2-cyanobenzyl-morpholinocarbothioate, S-2,6-dichlorobenzyl-N,N-dimethyl thiolcarbamate, S-4-chloro-2-methoxybenzyl-N-n-butyl-N-methyl thiolcarbamate, S-2-chloro-4-nitrobenzyl-N,N-pentamethylene thiolcarbamate, S-2,5-dimethylbenzyl-N,N-dimethyl thiolcarbamate and S-3,5-dinitrobenzyl-N,N-diethyl thiolcarbamate.

The reaction of the present invention is carried out as shown in the following reaction formula, by reacting carbonyl sulfide (II) with a sec-amine (I) to produce an aqueous solution of an amine salt of thiolcarbamic acid (III) and then, reacting a halogenated hydrocarbon (IV) with the amine salt.

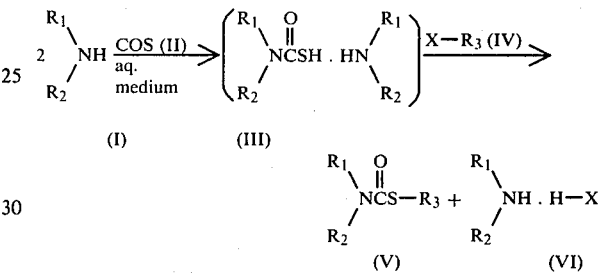

The reaction temperature in the reaction of carbonyl sulfide (II) with the sec-amine (I) is lower than 80° C. preferably 10° to 50° C.

The reaction temperature in the reaction of the halogenated hydrocarbon (IV) with the aqueous solution of amine salt of thiolcarbamic acid (III) is in a range of 0° to 80° C. preferably 20° to 60° C.

In both reactions, the amine salt of thiolcarbamic acid is not stable to be decomposed at higher than 80° C. disadvantageously.

The molar ratio of carbonyl sulfide (II) to the sec-amine (I) is less than 0.5 preferably less than 0.49.

When the molar ratio is higher than 0.5, the resulting amine salt of thiolcarbamic acid is unstable to be decomposed disadvantageously.

The molar ratio of the halogenated hydrocarbon (IV) to the amine salt of thiolcarbamic acid (III) in the aqueous solution thereof is preferably 1.0 as equi-mole.

The amount of the aqueous medium is preferably to give 40 to 80% especially 50 to 70% of the amine salt of thiolcarbamic acid (III) in the aqueous solution thereof.

When the aqueous medium is too much so as to give less than 40% of the amine salt of thiolcarbamic acid (III) in the aqueous solution thereof, the reaction of the halogenated hydrocarbon with the amine salt of thiolcarbamic acid is not smooth whereby the purity and yield of the object thiolcarbamate (V) are disadvantageously low.

When the aqueous medium is too small so as to give higher than 80% of the amine salt of thiolcarbamic acid (III) in the aqueous solution thereof, the amine salt of thiolcarbamic acid is unstable to be decomposed disadvantageously.

The reaction mixture of the thiolcarbamate (V), the sec-amine hydrohalide (VI) and water can be separated to the organic phase of thiolcarbamate (V) and the water phase of water and the sec-amine hydrohalide (VI) by the phase separation. The organic phase is treated by the conventional methods such as washing with water and distilling the object product to obtain the thiolcarbamate having high purity in high yield.

In the process of the present invention, it is usual not to use an organic solvent in the phase separation or in the water washing. However, if necessary, it is possible to use an organic solvent such as benzene, toluene, hexane, ether and chloroform.

The water phase of water and the sec-amine hydrohalide (VI) obtained by the phase separation is treated by the conventional methods such as neutralization and distillation, whereby the sec-amine (I) can be stoichiometrically recovered.

The feature of the process of the present invention is to obtain the thiolcarbamate having high purity in high yield in an aqueous medium without using a catalyst and an organic solvent. The disadvantages in the conventional processes are overcome and the thiolcarbamate having high purity is obtained in high yield without an environmental pollution and with low cost to attain significant advantages.

The process of the present invention will be further illustrated by certain examples and references.

EXAMPLE 1

Into a mixture of 146.3 g (2.0 mole) of diethylamine and 128.9 g of water under stirring, 58.9 g (0.98 mole) of carbonyl sulfide was fed at a reaction temperature of 15° to 20° C. to react them whereby 334.1 g of an aqueous solution of diethylamine salt of N,N-diethyl thiolcarbamic acid (59.9% (0.97 mole) of diethylamine salt of N,N-diethyl thiolcarbamic acid) was obtained and then, 156.2 g (0.97 mole) of 4-chlorobenzyl chloride was added dropwise to the aqueous solution under stirring at lower than 50° C. and the reaction was continued at 45° to 50° C. for 3 hours.

After the reaction, the resulting reaction mixture was separated to an organic phase and a water phase by the phase separation. The organic phase was washed with 500 ml of 1 N-HCl and then, it was further washed for two times with 500 ml of water and it was distilled to obtain 248.8 g of S-4-chlorobenzyl-N,N-diethyl thiolcarbamate having a boiling point of 126.0° to 127.0° C./0.008 mmHg (99.5% of yield based on 4-chlorobenzyl chloride).

The product was analyzed by a gas chromatography to show 98.95% of purity.

Reference

In a mixture of 73.1 g (1.0 mole) of diethylamine, 192.0 g (1.2 mole) of 25% aqueous solution of sodium hydroxide and 251.6 g of water, under stirring, 60.1 g (1.0 mole) of carbonyl sulfide was fed at a reaction temperature of 0° to 5° C. whereby an aqueous solution of sodium salt of N,N-diethyl thiolcarbamic acid was obtained and then, 161.0 g (1.0 mole) of 4-chlorobenzyl chloride was added dropwise at lower than 50° C. under stirring and the reaction was further continued at 45° to 50° C. for 3 hours.

After the reaction, the reaction mixture was treated in accordance with the process of Example 1 to obtain 214.2 g of S-4-chlorobenzyl-N,N-diethyl thiolcarbamate (83.1% of yield based on 4-chlorobenzyl chloride).

The product was analyzed by a gas chromatography to show 95.4% of purity.

When the reaction was continued for 24 hours. The yield was 90.2% and the purity was 95.5%.

EXAMPLES 2 TO 23

In accordance with the process of Example 1 except using 0.97 mole of each of various halogenated hydrocarbons (IV) instead of 156.2 g (0.97 mole) of 4-chlorobenzyl chloride, various thiolcarbamates (V) were produced.

The results are shown in Table 1 wherein the yield is based on the halogenated hydrocarbon (IV).

TABLE - 1

| Example | Starting materials | | Product | | |
|---|---|---|---|---|---|
| | Sec-amine (I) | Halogenated hydrocarbon (IV) | Thiolcarbamate (V) | b.p. (°C./mmHg) | Yield (%) |
| 2 | $(C_2H_5)_2NH$ | $ClCH_2$—⟨C₆H₅⟩ | $(C_2H_5)_2NC(O)SCH_2$—⟨C₆H₅⟩ | 100–110/0.02 | 99.4 |
| 3 | " | $ClCH_2$—⟨C₆H₄⟩—F | $(C_2H_5)_2NC(O)SCH_2$—⟨C₆H₄⟩—F | 102–110/0.02 | 99.2 |
| 4 | " | $BrCH_2$—⟨C₆H₄⟩—Br | $(C_2H_5)_2NC(O)SCH_2$—⟨C₆H₄⟩—Br | 139–140/0.005 | 99.3 |
| 5 | " | $ClCH_2$—⟨C₆H₄⟩—I | $(C_2H_5)_2NC(O)SCH_2$—⟨C₆H₄⟩—I | 150/0.08 over | 99.2 |
| 6 | " | $ClCH_2$—⟨C₆H₄⟩—$C_2H_5$ | $(C_2H_5)_2NC(O)SCH_2$—⟨C₆H₄⟩—$C_2H_5$ | 130–132/0.08 | 99.0 |
| 7 | " | $ClCH_2$—⟨C₆H₄⟩—(i-$C_3H_7$) | $(C_2H_5)_2NC(O)SCH_2$—⟨C₆H₄⟩—(i-$C_3H_7$) | 127–128/0.03 | 98.8 |
| 8 | " | $ClCH_2$—⟨C₆H₄⟩—$OCH_3$ | $(C_2H_5)_2NC(O)SCH_2$—⟨C₆H₄⟩—$OCH_3$ | 151–152/0.4 | 98.7 |

TABLE 1-continued

| | Starting materials | | Product | | |
|---|---|---|---|---|---|
| Example | Sec-amine (I) | Halogenated hydrocarbon (IV) | Thiolcarbamate (V) | b.p. (°C./mmHg) | Yield (%) |
| 9 | " | ClCH$_2$–C$_6$H$_4$–O(i-C$_3$H$_7$) | (C$_2$H$_5$)$_2$NC(O)SCH$_2$–C$_6$H$_4$–O(i-C$_3$H$_7$) | 162–163/11 | 98.9 |
| 10 | " | ClCH$_2$–C$_6$H$_4$–SCH$_3$ | (C$_2$H$_5$)$_2$NC(O)SCH$_2$–C$_6$H$_4$–SCH$_3$ | 154–158/0.01 | 98.9 |
| 11 | " | ClCH$_2$–C$_6$H$_4$–SC$_2$H$_5$ | (C$_2$H$_5$)$_2$NC(O)SCH$_2$–C$_6$H$_4$–SC$_2$H$_5$ | 153–157/0.08 | 98.7 |
| 12 | " | BrCH$_2$–C$_6$H$_4$(NO$_2$) | (C$_2$H$_5$)$_2$NC(O)SCH$_2$–C$_6$H$_4$(NO$_2$) | 142–148/0.015 | 99.2 |
| 13 | " | BrCH$_2$–C$_6$H$_4$(CN) | (C$_2$H$_5$)$_2$NC(O)SCH$_2$–C$_6$H$_4$(CN) | 143–165/0.002 | 98.4 |
| 14 | " | ClCH$_2$–C$_6$H$_3$(Cl)(Cl) | (C$_2$H$_5$)$_2$NC(O)SCH$_2$–C$_6$H$_3$(Cl)(Cl) | 148–152/0.05 | 99.2 |
| 15 | " | ClCH$_2$–C$_6$H$_3$(Cl)(CH$_3$) | (C$_2$H$_5$)$_2$NC(O)SCH$_2$–C$_6$H$_3$(Cl)(CH$_3$) | 135–143/0.015 | 98.8 |
| 16 | " | ClCH$_2$–C$_6$H$_3$(Cl)(O(n-C$_4$H$_9$)) | (C$_2$H$_5$)$_2$NC(O)SCH$_2$–C$_6$H$_3$(Cl)(O(n-C$_4$H$_9$)) | 176–181/0.1 | 98.7 |
| 17 | " | ClCH$_2$–C$_6$H$_3$(OCH$_3$)(Br) | (C$_2$H$_5$)$_2$NC(O)SCH$_2$–C$_6$H$_3$(OCH$_3$)(Br) | 154–155/0.07 | 98.5 |
| 18 | " | ClCH$_2$–C$_6$H$_3$(SCH$_3$)(Cl) | (C$_2$H$_5$)$_2$NC(O)SCH$_2$–C$_6$H$_3$(SCH$_3$)(Cl) | 162–166/0.05 | 98.6 |
| 19 | " | ClCH$_2$–C$_6$H$_3$(NO$_2$)(Cl) | (C$_2$H$_5$)$_2$NC(O)SCH$_2$–C$_6$H$_3$(NO$_2$)(Cl) | 170/0.02 over | 99.4 |
| 20 | " | ClCH$_2$–C$_6$H$_3$(CH$_3$)(OCH$_3$) | (C$_2$H$_5$)$_2$NC(O)SCH$_2$–C$_6$H$_3$(CH$_3$)(OCH$_3$) | 155–157/0.2 | 98.5 |
| 21 | " | ClCH$_2$–C$_6$H$_3$(CH$_3$)(OC$_2$H$_5$) | (C$_2$H$_5$)$_2$NC(O)SCH$_2$–C$_6$H$_3$(CH$_3$)(OC$_2$H$_5$) | 159–162/0.12 | 98.3 |
| 22 | " | ClCH$_2$–C$_6$H$_3$(SCH$_3$)(CH$_3$) | (C$_2$H$_5$)$_2$NC(O)SCH$_2$–C$_6$H$_3$(SCH$_3$)(CH$_3$) | 165–170/0.2 | 98.4 |
| 23 | " | IC$_2$H$_5$ | (C$_2$H$_5$)$_2$NC(O)SC$_2$H$_5$ | 51–53/0.5 | 98.0 |

EXAMPLE 24 TO 41

In a mixture of 1 mole of each of various sec-amine (I) and 109.6 g of water (70.0 g of water in Examples 24, 35 and 38) under stirring, 0.49 mole of carbonyl sulfide was fed at a reaction temperature of lower than 50° C. to react them whereby the specific concentrations of aqueous solutions of each of various amine salts of thiolcarbamic acid (III) were obtained and then, each of various halogenated hydrocarbons (IV) was added to the aqueous solution at lower than 60° C. to react them at the specific temperature, and it was treated in accordance with the process of Example 1 to obtain various thiolcarbamates (V).

The results are shown in Table 2 wherein the yield is based on the halogenated hydrocarbon (IV).

TABLE - 2

| Example | Starting materials | | | Reaction condition | | Product | | |
|---|---|---|---|---|---|---|---|---|
| | Sec-amine (I) | Concentration of aq. sol. of amine salt of thiolcarbamic acid (%) | Halogenated hydrocarbon (IV) | Temp. (°C.) | Time (hr.) | Thiolcarbamate (V) | b.p. (°C./mmHg) | Yield (%) |
| 24 | $(CH_3)_2NH$ | 50.9 | $ClCH_2$-C$_6$H$_4$-$SC_2H_5$ | 20 | 8 | $(CH_3)_2NC(O)SCH_2$-C$_6$H$_4$-$SC_2H_5$ | 145–150/0.08 | 98.3 |
| 25 | $(n-C_3H_7)_2NH$ | 53.5 | $ClCH_2$-C$_6$H$_3$(Cl)(OCH$_3$) | 55–60 | 8 | $(n-C_3H_7)_2NC(O)SCH_2$-C$_6$H$_3$(Cl)(OCH$_3$) | 190–195/0.015 | 98.2 |
| 26 | " | 53.5 | $ICH_2C_2H_5$ | 40–45 | 6 | $(n-C_3H_7)_2NC(O)SCH_2C_2H_5$ | 100–115/10 | 97.2 |
| 27 | $(i-C_3H_7)_2NH$ | 53.4 | $ClCH_2$-C$_6$H$_4$-Cl | 45–50 | 3 | $(i-C_3H_7)_2NC(O)SCH_2$-C$_6$H$_4$-Cl | 142–146/0.04 | 99.4 |
| 28 | $(n-C_4H_9)_2NH$ | 58.2 | $ClCH_2$-C$_6$H$_4$-$(i-C_3H_7)$ | 45–50 | 4 | $(n-C_4H_9)_2NC(O)SCH_2$-C$_6$H$_4$-$(i-C_3H_7)$ | 155–159/0.04 | 98.2 |
| 29 | $(i-C_4H_9)_2NH$ | 58.3 | $BrCH_2$-C$_6$H$_4$-CN | 45–50 | 4 | $(i-C_4H_9)_2NC(O)SCH_2$-C$_6$H$_4$-CN | 156–157/0.008 | 97.3 |
| 30 | $(n-C_8H_{17})_2NH$ | 69.9 | $ClCH_2$-C$_6$H$_4$-$NO_2$ | 45–50 | 4 | $(n-C_8H_{17})_2NC(O)SCH_2$-C$_6$H$_4$-$NO_2$ | 167–180/0.01 | 97.4 |
| 31 | $(CH_2=CHCH_2)_2NH$ | 52.8 | $ClCH_2$-C$_6$H$_4$-$C_2H_5$ | 40–45 | 6 | $(CH_2=CH-CH_2)_2NC(O)SCH_2$-C$_6$H$_4$-$C_2H_5$ | 144–145/0.02 | 98.5 |
| 32 | $(HOC_2H_4)_2NH$ | 54.3 | $ClCH_2$-C$_6$H$_4$-$NO_2$ | 55–60 | 6 | $(HOC_2H_4)_2NC(O)SCH_2$-C$_6$H$_4$-$NO_2$ | 150/0.08 over | 98.2 |
| 33 | $C_6H_5$-$(CH_2)_2$NH | 66.2 | $ClCH_2$-C$_6$H$_4$-$C_2H_5$ | 40–45 | 6 | $C_6H_5$-$(CH_2)_2NC(O)SCH_2$-C$_6$H$_4$-$C_2H_5$ | 200–205/0.1 | 97.3 |
| 34 | $CH_3(n-C_4H_9)NH$ | 50.8 | $ClCH_2$-C$_6$H$_4$-$OCH_3$ | 30–35 | 6 | $CH_3(n-C_4H_9)NC(O)SCH_2$-C$_6$H$_4$-$OCH_3$ | 147–150/0.1 | 97.3 |

TABLE-2-continued

| Example | Starting materials | | | Reaction condition | | Product | | Yield (%) |
|---|---|---|---|---|---|---|---|---|
| | Sec-amine (I) | Concentration of aq. sol. of amine salt of thiolcarbamic acid (%) | Halogenated hydrocarbon (IV) | Temp. (°C.) | Time (hr.) | Thiolcarbamate (V) | b.p. (°C./mmHg) | |
| 35 | CH₃—NH—OCH₃ | 55.6 | ClCH₂—C₆H₃(Cl)(Cl) (2,5-dichlorobenzyl) | 45-50 | 3 | CH₃(CH₃O)N-C(O)-SCH₂-C₆H₃(Cl)(Cl) | 137/0.05 | 99.4 |
| 36 | CH₃(C₆H₅)NH | 54.6 | ClCH₂—C₆H₄—C₂H₅ | 40-45 | 6 | CH₃(C₆H₅)N-C(O)-SCH₂-C₆H₄-C₂H₅ | 162/0.02 | 98.2 |
| 37 | C₂H₅(C₆H₅)NH | 57.0 | ClCH₂—C₆H₄—(i-C₃H₇) | 40-45 | 6 | C₂H₅(C₆H₅)N-C(O)-SCH₂-C₆H₄-(i-C₃H₇) | 166-168/0.04 | 97.3 |
| 38 | pyrrolidine-NH | 58.1 | ClCH₂—C₆H₄—OCH₃ | 30-35 | 6 | pyrrolidine-N-C(O)-SCH₂-C₆H₄-OCH₃ | 170-173/0.2 | 97.4 |
| 39 | piperidine-NH | 50.3 | ClCH₂—C₆H₄—SCH₃ | 55-60 | 8 | piperidine-N-C(O)-SCH₂-C₆H₄-SCH₃ | 182-187/0.4 | 97.2 |
| 40 | hexamethyleneimine-NH | 53.2 | ClCH₂—C₆H₃(CH₃)(CH₃) | 45-50 | 8 | hexamethyleneimine-N-C(O)-SCH₂-C₆H₃(CH₃)(CH₃) | 164-169/0.3 | 98.4 |
| 41 | morpholine-NH | 50.8 | ClCH₂—C₆H₃(Cl)(NO₂) | 50-55 | 3 | morpholine-N-C(O)-SCH₂-C₆H₃(Cl)(NO₂) | 170/0.08 over | 99.3 |

What is claimed is:

1. In a process for producing a thiolcarbamate having the formula:

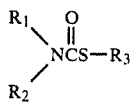

wherein $R_1$ and $R_2$ are the same or different and each represents an alkyl, alkoxy, alkenyl, cycloalkyl, hydroxyalkyl, phenyl or benzyl group and $R_1$ and $R_2$ can form a pyrrolidinyl, piperidyl, morpholino or hexamethyleneimino ring and $R_3$ represents a lower alkyl or benzyl group or a substituted benzyl group having one or two halogen atom, alkyl, alkoxy, alkylthio, nitro or cyano group substituents by reacting carbonyl sulfide with a sec-amine having the formula:

wherein $R_1$ and $R_2$ are as defined above thereby forming an amine salt of a thiolcarbamic acid having the formula:

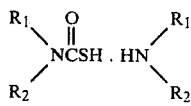

and then reacting said salt with a halogenated hydrocarbon having the formula:

wherein $R_3$ is as defined above and X represents a halogen atom, the improvement comprising: conducting said reaction between said sec-amine and said carbonyl sulfide in a solvent consisting of water thereby forming an aqueous solution of said salt having a salt concentration ranging from 40 to 80%; and thereafter reacting said salt with said halogenated hydrocarbon.

2. The process according to claim 1, wherein the reaction temperature in both of the reactions is less than 80° C.

3. The process according to claim 1, wherein the molar ratio of carbonyl sulfide to the sec-amine (I) is less than 0.5.

4. The process according to claim 3, wherein the molar ratio of the carbonyl sulfide to the sec-amine (I) is less than 0.49.

5. The process according to claim 1, wherein the concentration of said amine salt of thiolcarbamic acid (III) in the aqueous solution in the first reaction ranges from 40% to 80%.

6. The process according to claim 1, wherein the concentration of said amine salt of thiolcarbamic acid in the aqueous solution at the beginning of the second reaction is in a range of 40 to 80%.

7. The process according to claim 1, wherein said secondary amine is a member selected from the group consisting of dimethylamine, diethylamine, di-n-propylamine, di-iso-propylamine, di-n-butylamine, di-iso-butylamine, di-n-amylamine, di-n-hexylamine, bis(2-ethylhexyl)amine, di-n-octylamine, diallylamine, bis(2-methylallyl)amine, dicyclohexylamine, diethanolamine, di-iso-propanolamine, diphenylamine, dibenzylamine, N-methyl-n-butylamine, N-ethyl-n-butylamine, N-butylethanolamine, N-methyl phenylamine, N-ethyl phenylamine, N-methyl benzylamine, N-ethyl benzylamine, N-methyl cyclohexylamine, pyrrolidine, piperidine, hexamethyleneimine and morpholine.

8. The method according to claim 1, wherein said halogenated hydrocarbon is methyl iodide, ethyl iodide, isopropyl iodide, n-propyl bromide, n-butyl iodide, iso-butyl bromide, benzyl chloride, benzyl bromide, benzyl iodide, 2-, 3- or 4-fluorobenzyl chloride or bromide, 2-, 3- or 4-chlorobenzyl chloride or bromide, 2-, 3- or 4-bromobenzyl bromide, 2-, 3- or 4-iodobenzyl chloride, 2-, 3-, or 4-methylbenzyl chloride or bromide, 4-ethylbenzyl chloride, 4-(isopropyl)benzyl chloride, 4-(isopropyl)-benzyl bromide, 2-methoxybenzyl chloride, 3-ethoxybenzyl bromide, 4-(isopropoxy) benzyl chloride, 4-methylthiobenzyl chloride, 4-ethylthiobenzyl chloride, 2-, 3- or 4-nitrobenzyl chloride or bromide, 2-, 3- or 4-cyanobenzyl bromide, 2,6-dichlorobenzyl chloride or bromide, 4-chloro-2-methoxybenzyl chloride, 2-chloro-4-nitrobenzyl chloride or bromide, 2,5-dimethylbenzyl chloride, 4-methyl-3-nitrobenzyl chloride or 3,5-dinitrobenzyl chloride.

9. The method of claim 1, wherein the reaction between carbonyl sulfide and said secondary amine is conducted at a temperature from 10°–50° C.

10. The method according to claim 1, wherein the reaction between said halogenated hydrocarbon and said amine salt of thiolcarbamic acid is conducted at a temperature from 20°–60° C.

* * * * *